(12) United States Patent
Prestel

(10) Patent No.: US 8,398,674 B2
(45) Date of Patent: Mar. 19, 2013

(54) MEDICAL INSTRUMENT WITH MULTI-JOINT ARM

(75) Inventor: Stephan Prestel, Rheinstetten-Mörsch (DE)

(73) Assignee: Richard Wolf GmbH, Knittlingen (DE)

( * ) Notice: Subject to any disclaimer, the term of this patent is extended or adjusted under 35 U.S.C. 154(b) by 177 days.

(21) Appl. No.: 12/886,885

(22) Filed: Sep. 21, 2010

(65) Prior Publication Data

US 2011/0071561 A1   Mar. 24, 2011

(30) Foreign Application Priority Data

Sep. 21, 2009  (DE) .................. 10 2009 042 411

(51) Int. Cl.
*A61B 17/00* (2006.01)
(52) U.S. Cl. ......... 606/208; 606/170; 606/174; 606/205
(58) Field of Classification Search .................. 606/170, 606/174, 205–208, 1; 227/175.1, 178.1, 227/179.1, 181.1, 182.1, 176.1, 180.1, 19; 81/314, 342, 345; 294/100, 119, 209, 210, 294/211
See application file for complete search history.

(56) References Cited

U.S. PATENT DOCUMENTS

| | | | | |
|---|---|---|---|---|
| 5,330,502 A | * | 7/1994 | Hassler et al. | 606/205 |
| 5,374,277 A | * | 12/1994 | Hassler | 606/207 |
| 5,607,450 A | * | 3/1997 | Zvenyatsky et al. | 606/206 |
| 6,592,572 B1 | * | 7/2003 | Suzuta | 606/1 |
| 7,288,103 B2 | | 10/2007 | Suzuki | |
| 7,476,237 B2 | * | 1/2009 | Taniguchi et al. | 606/205 |
| 7,494,499 B2 | * | 2/2009 | Nagase et al. | 606/205 |
| 7,666,206 B2 | * | 2/2010 | Taniguchi et al. | 606/206 |
| 2004/0193212 A1 | * | 9/2004 | Taniguchi et al. | 606/205 |
| 2004/0249411 A1 | * | 12/2004 | Suzuki | 606/205 |
| 2006/0259071 A1 | * | 11/2006 | Nicholas et al. | 606/205 |
| 2008/0039892 A1 | * | 2/2008 | Mitsuishi et al. | 606/208 |

FOREIGN PATENT DOCUMENTS

DE   93 20 558 U1   11/1994
EP   1 679 042 A1   7/2006

OTHER PUBLICATIONS

German Examination Report issued on Jul. 19, 2010 in German Application No. 10 2009 042 411.3.

* cited by examiner

*Primary Examiner* — Ryan Severson
*Assistant Examiner* — David Eastwood
(74) *Attorney, Agent, or Firm* — Panitch Schwarze Belisario & Nadel LLP

(57) ABSTRACT

A medical instrument includes a hollow shank and an instrument section arranged pivotable to the hollow shank proximate the distal end of this hollow shank. An instrument part is mounted in an axially movable manner in the pivotable instrument section. This instrument part, which may be a part acting in a direct manner on organs, tissue or the like, or preferably serves for movement coupling to such a part in the pivotable instrument section, is coupled in movement via a forcibly guided multi joint arm to an actuator, which is axially movably guided in the hollow shank

9 Claims, 6 Drawing Sheets

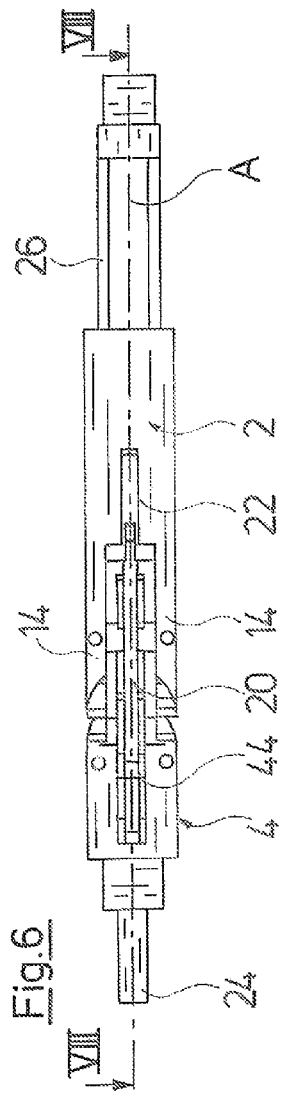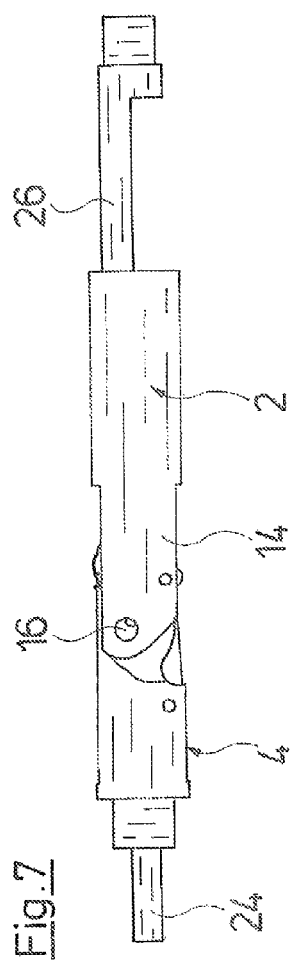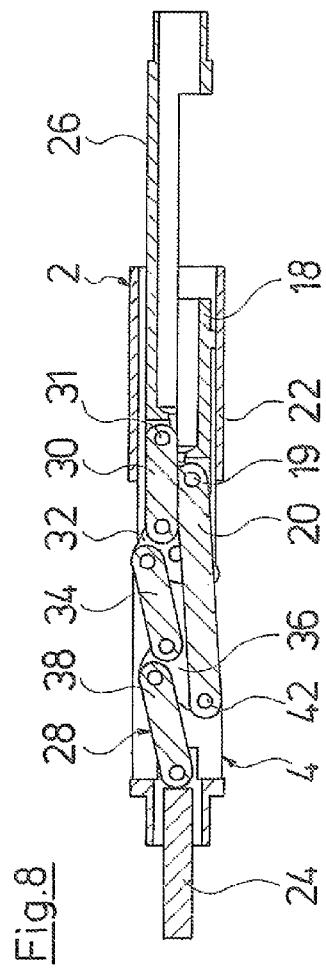

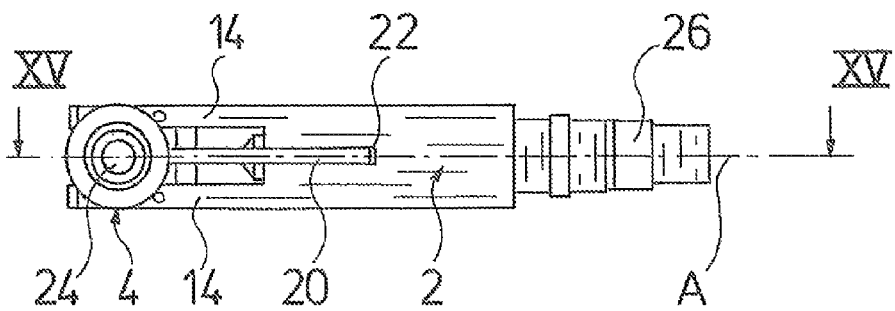
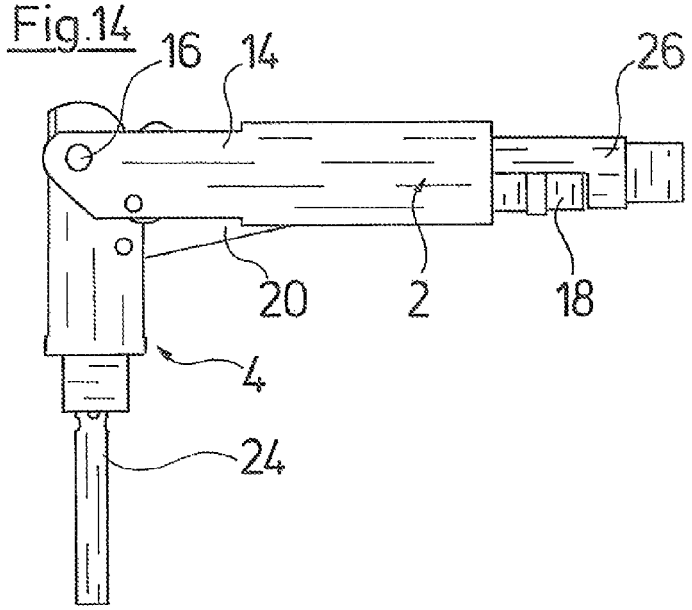
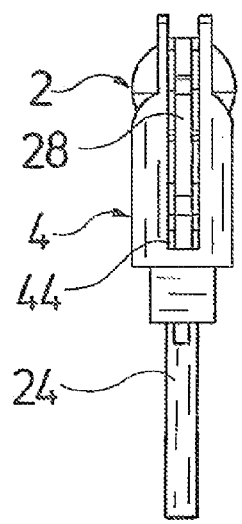
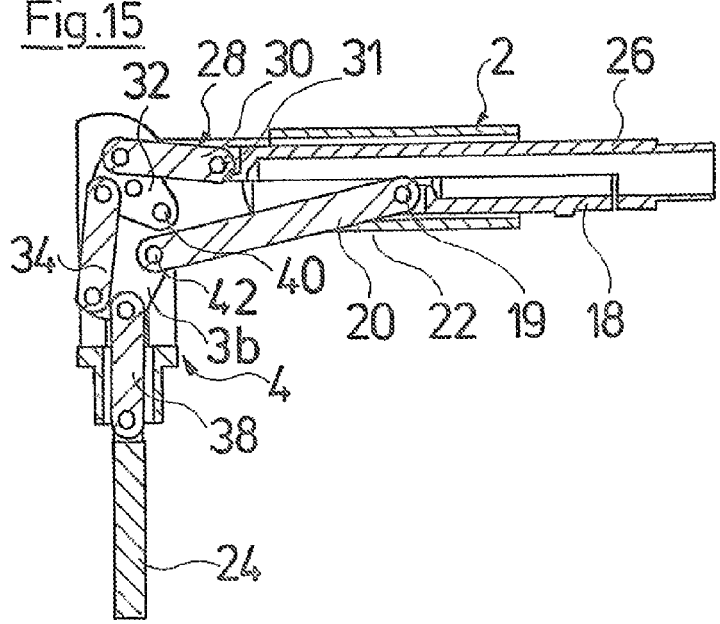

MEDICAL INSTRUMENT WITH MULTI-JOINT ARM

BACKGROUND OF THE INVENTION

The invention relates to a medical instrument having a hollow shank and an instrument section including an instrument part movably mounted in the instrument section, wherein the instrument section is arranged close to the distal end of the hollow shank and in a pivotable manner to the hollow shank, Hollow-shank instruments, such as manipulators, forceps or scissors are known for endoscopic application, with which movable instrument parts arranged at the distal end of a hollow shank are coupled in movement via an actuation element, which is axially movably guided in the hollow shank, to a handle arranged at the proximal end of the hollow shank, and thus may be operated. Instruments have been developed which, distally of the hollow shank, comprise an end piece, which is pivotable relative to the straight hollow shank in order, via an access channel into the inside of a body, to also be able to reach those treatment regions which lie laterally of an access axis defined by the access channel. However, with these instruments, and with a pivoted (angled) end piece, the force transmission from the handle to the movable instrument part on the pivotable end piece has been found to be problematic, since only relatively small forces may be transmitted by an actuation element in the hollow shank to the movable instrument part.

It is known to use control wires, which are typically fastened on the end piece distally spaced from a pivot axis of this end piece and which are led through the hollow shank to the proximal-end handle for actuation, for pivoting the pivotable distal end piece of these instruments. The pivoting ability of the end-piece is limited, however, due to the fact that the control wires, which bend transversely to their longitudinal axis with the pivoting of the end-piece, may not be bent up to a kinking limit, since the end-piece may no longer be pivoted back if the control wire is kinked. Insofar as this is concerned, the end-pieces of these instruments may only be pivoted within a comparatively small angular range.

BRIEF SUMMARY OF THE INVENTION

It is an object of the invention to provide a medical instrument of the type mentioned above, having a hollow shank and an instrument section, which is pivotably arranged in the region of the distal end of the hollow shank, wherein the medical instrument, given a pivoted instrument section, permits an efficient force transmission from a handle arranged at the proximal end of the shank to the instrument part, which is movably guided on the pivotable instrument section. In a further embodiment of the invention the pivotable instrument section may be pivoted in a larger angular range than with instruments of this type which have been known until now.

This object is achieved by a medical instrument of the type mentioned at the outset, wherein the instrument part is coupled in movement to an actuator which is axially movably guided in the hollow shank via a forcibly guided multi-joint arm. Advantageous further embodiments of this instrument are to be deduced from the following description as well as the drawings. Here, according to the invention, features specified in the description in each case on their own, but also in combination, may further form the inventive solution.

The medical instrument according to the invention comprises a hollow shank. An instrument section is arranged in a manner such that it may be pivoted away from the hollow shank, in the vicinity of the distal end of this hollow shank. An instrument part is mounted in an axially movable manner in the pivotable instrument section. This instrument part, which may also be a part with which one may act directly on organs, tissue and the like, or preferably serves for the movement coupling to such a part in the pivotable instrument section, is coupled in movement via a forcibly guided multi-joint arm to an actuator which is guided in an axially movable manner in the hollow shank.

The multi-joint arm usefully comprises several rigid arm parts, which are connected to one another in an articulated manner in series. In this context, a multi-joint arm is also to be understood as a pintle chain as is used, for example, in chain drives. With the joint-arm the invention provides for a connection element between the actuator arranged in the hollow shank and the moveably mounted instrument part, which is arranged in the pivotable instrument section, and this connection element may be angled in a manner adapted to a pivoting of the pivotable instrument section.

Due to the forced guiding, the pivoting of the individual arm parts of the multi-joint arm is defined when pivoting the pivotable instrument section, and in cooperation with the selection of a suitable number of arm parts and suitable arm part dimensions, may advantageously be selected such that the multi-joint arm, at least for the most part, is arranged within the inner cross section of the hollow shank and pivotable instrument section, during the pivoting and after the pivoting, and a particularly efficient force transmission is made possible from the actuator guided in the hollow shank to the instrument part which is movably mounted in the pivotable instrument section. Advantageously, the multi-joint arm may transmit compression forces and tensile forces from the actuator onto the instrument part movably mounted in the pivotable instrument section, to the same extent even in the bent condition.

The actuator, which is guided in the hollow shank in the axial direction of the shank, may usefully be designed in a manner such that it may be operated from a handle arranged on the proximal end of the hollow shank.

The multi-joint arm may advantageously comprise at least three arm parts, which are connected to one another in an articulated manner in series, wherein at least one arm part arranged between two arm parts, may be pivotable about an axis which is arranged on the hollow shank and spaced from a straight connection line of the articulation points of adjacent arm parts to this middle arm part. Thus, a second arm part may be articulated on a first arm part, which is articulated on the actuator led in the hollow shank, spaced from the articulation to the actuator, and this second arm part in turn is connected in an articulated manner to a third arm part, spaced from the articulated connection to the first arm part, wherein the instrument part which is movably mounted in the pivotable instrument section is articulated on the third arm part at a spacing from the articulated connection to the second arm part. With this design, the second arm part forms a lever arm which is aligned normally to the connection line of the articulation points of the second arm part to the first and third arm parts, and this lever arm is pivotably articulated on the hollow shank in the region of its end which is away from the connection line of the articulation points to the adjacent arm parts. Insofar as this is concerned, the possible movement path of the second arm part is defined, and the multi-joint arm, comprising the first, second and third arm parts, is forcibly guided.

A particularly effective force transmission from the actuator guided in the hollow shank to the instrument part movably mounted in the pivotable instrument section, and a bending of the multi-joint part which is adapted as tightly as possible to the pivoting of the pivotable instrument section, may be achieved if, as is further advantageously envisaged, additionally to the forced guiding on the hollow shank, at least one further arm part arranged between two arm parts is pivotable about an axis which however is advantageously arranged on the pivotable instrument section, spaced from a straight connection line of the articulation points of adjacent arm parts to this arm part. Here, the arm part which is articulated on the pivotable instrument section forms a further forced guiding of the multi joint arm on the pivotable instrument section. Accordingly, the multi-joint arm, with this design, is forcibly guided on the hollow shank as well as on the pivotable instrument section. Usefully, the multi-joint arm here comprises at least five arm parts, wherein the arm part which forms the forced guiding on the pivotable instrument section, is typically not directly connected to the arm part forming the forced guiding on the hollow shank.

For pivoting the pivotable instrument section relative to the hollow shank, one preferably envisages a lever, which is articulated on a distal end region of a second actuator led in an axially movable manner in the hollow shank, and on the pivotable instrument section. That is, the second axially movable actuator, with the lever and the pivotable instrument section, forms a slider-crank-like mechanism, with which the linear movement of the actuator arranged in the hollow shank is converted into a pivot movement of the pivotable instrument section. By way of this mechanism, the pivotable instrument section may be pivoted in a significantly larger angular range than was the case with the instruments known until now, which used control wires for pivoting a distal instrument section. In order to permit the pivoting of the lever articulated on the actuator, it may be useful to provide the hollow shank with a longitudinal slot at its distal end opposite the lever.

Usefully, the hollow shank may be designed such that its distal end forms a fork, on which the pivotable instrument section is articulated. Then, two continuations which extend in the longitudinal direction of the tube and lie directly opposite one another on the tube, may be formed at the distal end of a rigid tube forming the hollow shank. The pivotable instrument section may be mounted in a pivotable manner between these continuations, wherein the articulation of the pivotable instrument section is preferably effected at two pins, which, at the inner sides of the continuations of the hollow shank, the inner sides facing one another, project in the direction of a central axis of the hollow shank, in a manner such that they form a common pivot axis for the pivotable instrument section. The continuations which are formed on the hollow shank are favorably dimensioned, such that they permit a pivoting of the pivotable instrument section in an angular range of about 90° transversely to the central axis of the hollow shank, so that with the instrument according to this embodiment of the invention, organ and tissue manipulation is possible laterally and even transversely to the access channel, via which the instrument is led into the inside of the body.

Preferably, a tube part forms an outer envelope of the pivotable instrument section. The instrument part of the pivotable instrument section, which is coupled in movement to the multi-joint arm, may be movably mounted in this tube part. Moreover, this tube part may serve for receiving a part of the multi-joint arm. In order to be able to deflect its arm parts arranged in the tube part, with a bending of the multi-joint arm even beyond the inner contour of the tube part, the tube part may be designed in a longitudinally slotted manner in a region lying directly opposite the multi-joint arm, i.e., a region which lies directly outside the multi-joint arm.

With regard to the medical instrument according to an embodiment of the invention, it is preferably the case of such an instrument which comprises a distal instrument jaw having two branches which may be moved relative to one another. Thus, the instrument according to an embodiment of the invention may be a gripper forceps or a scissors, wherein at least one branch is coupled in movement to the instrument part which is movably mounted in the pivotable instrument section. Moreover, the instrument according to an embodiment of the invention may preferably also be an organ manipulator having a spreading body, which may spread open in a fan-like manner and which is arranged at the distal side, wherein individual or several spreading arms of the spreading body are coupled in movement to the instrument part which is movably mounted in the pivotable instrument section.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 6 is an underside view of the distal end region in a second working position of the medical instrument according to FIG. 3;

FIG. 7 is a lateral view of the distal end region of the medical instrument according to FIG. 6;

FIG. 8 is a sectional view along line VIII-VIII in FIG. 6;

FIG. 13 is an underside view of the distal end region in a fourth working position of the medical instrument according to FIG. 3;

FIG. 14 is a lateral view of the distal end region of the medical instrument according to FIG. 13;

FIG. 15 is a sectional view along line XV-XV in FIG. 13; and

FIG. 16 is a front view of a distal end region of the medical instrument according to FIG. 13.

DETAILED DESCRIPTION OF THE INVENTION

Figure 1:
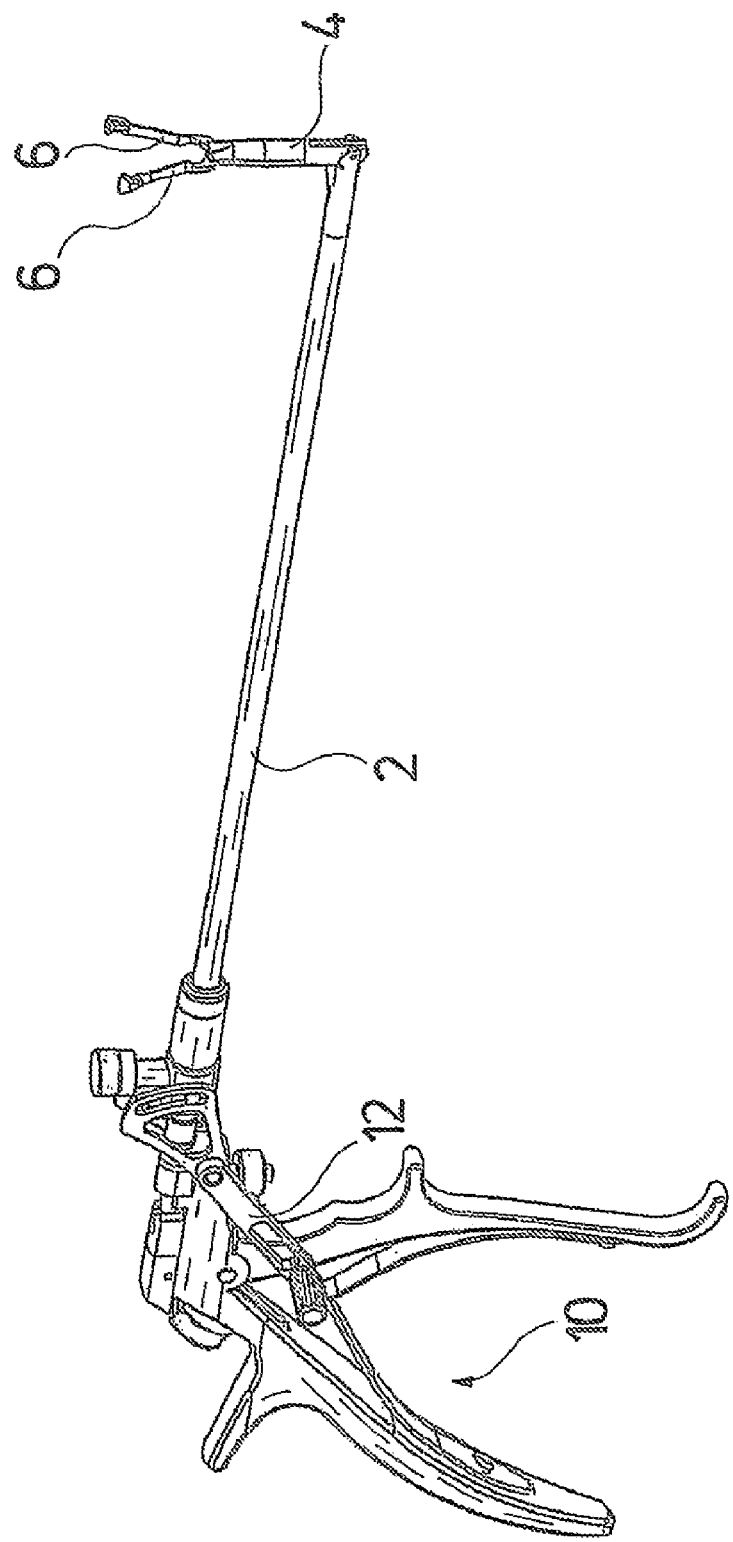
FIG. 1 is a schematic perspective view of a medical gripper forceps according to one embodiment of the invention.
Figure 2:
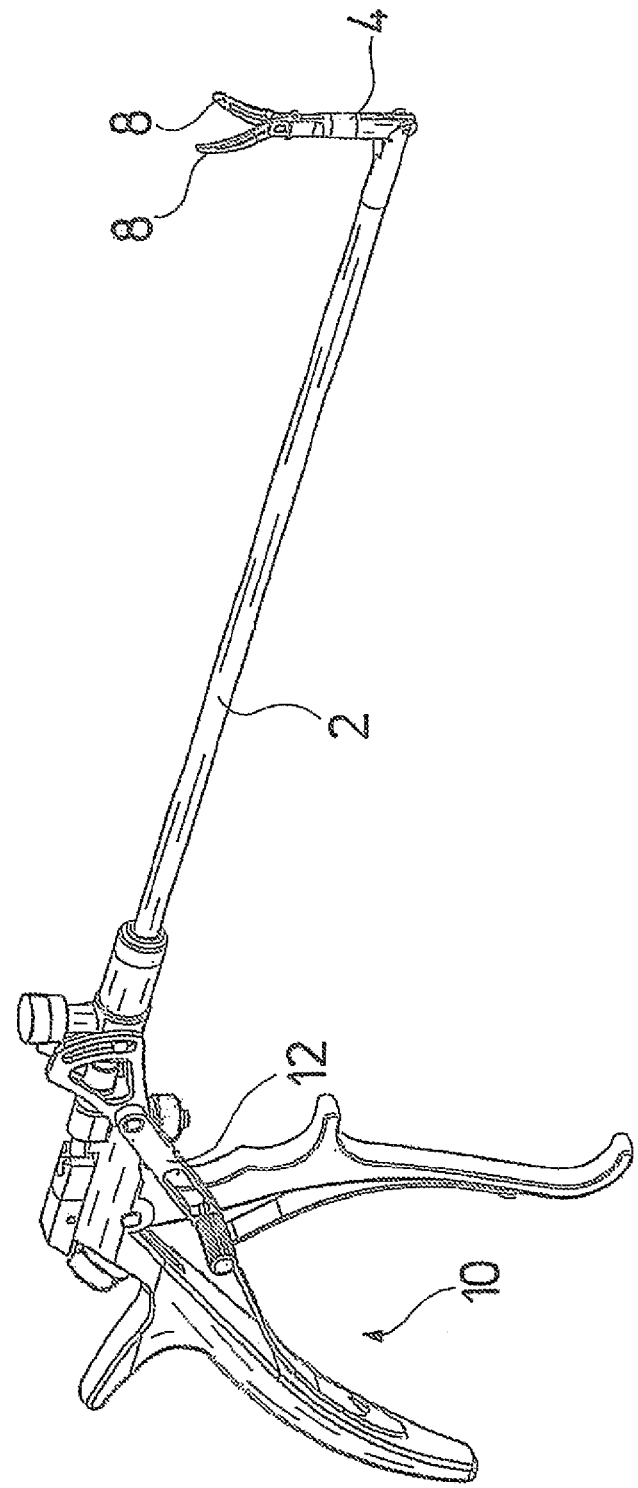
FIG. 2 is a schematic perspective view of a medical scissors according to another embodiment of the invention.
Figure 3:
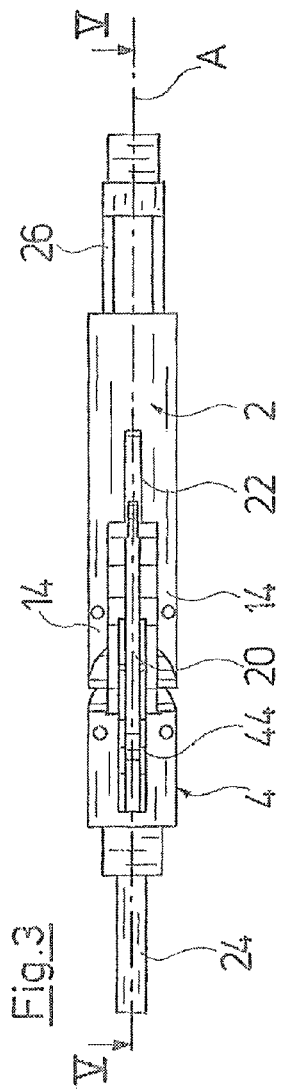
FIG. 3 is an underside view of a distal end region in a first working position of a medical instrument according to an embodiment of the invention having a pivotable instrument section.
Figure 4:
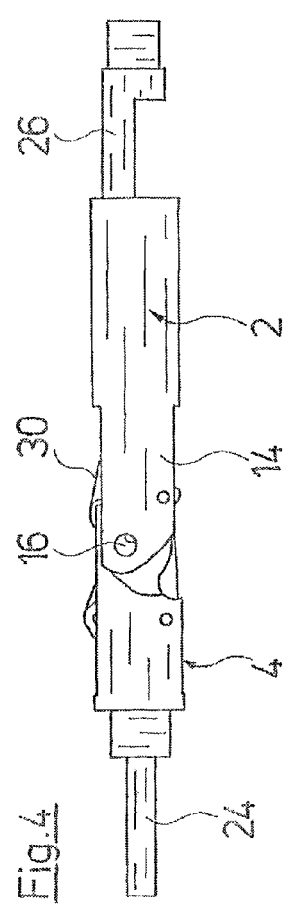
FIG. 4 is a lateral view of the distal end region according to FIG. 3.
Figure 5:
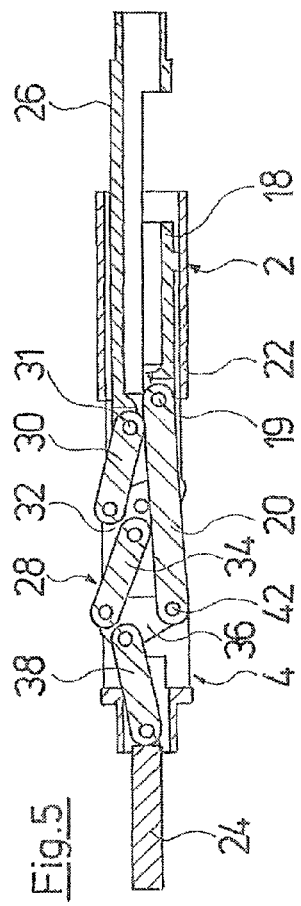
FIG. 5 is a sectional view along line V-V in FIG. 3.
Figure 9:
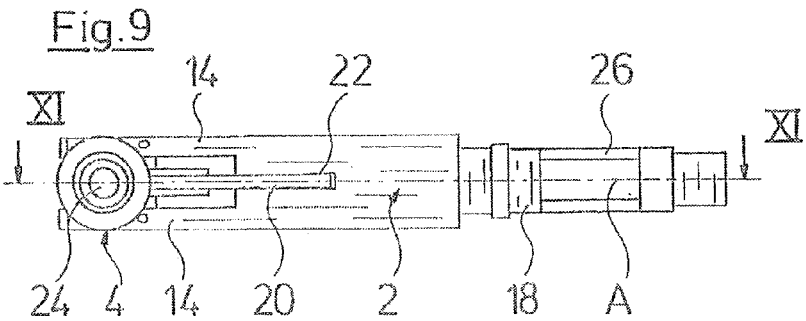
FIG. 9 is an underside view of the distal end region in a third working position of the medical instrument according to FIG. 3.
Figure 10:
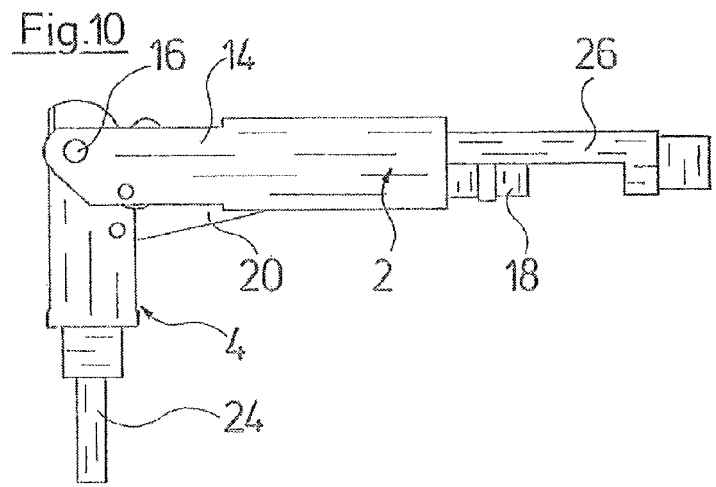
FIG. 10 is a lateral view of the distal end region of the medical instrument according to FIG. 9.
Figure 12:
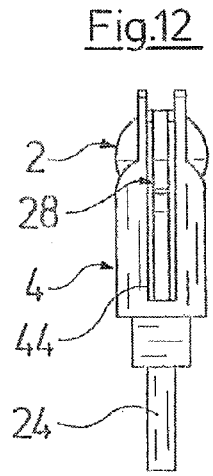
FIG. 12 is a front view of the distal end region of the medical instrument according to FIG. 9.
Figure 11:
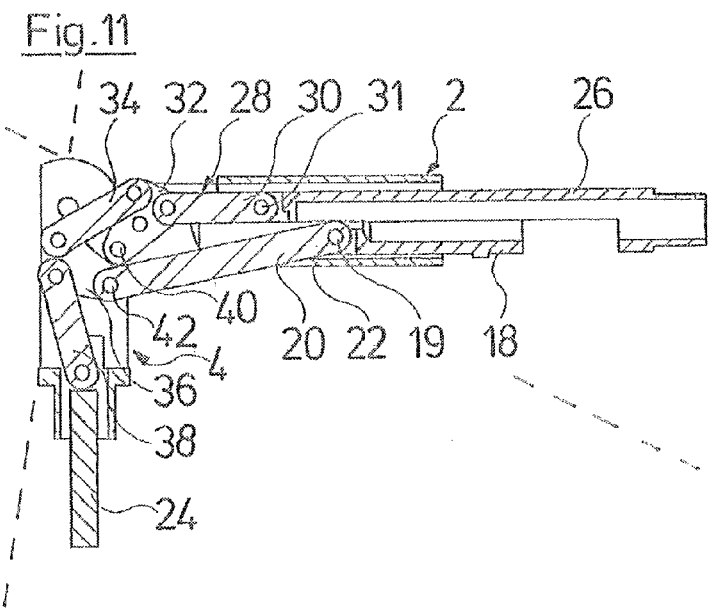
FIG. 11 is a sectional view along line XI-XI in FIG. 9.

The medical gripper forceps represented in FIG. 1 and the medical scissors represented in FIG. 2 respectively comprise a hollow shank 2, which is formed of a rigid, straight tube. In the vicinity of the distal end of the hollow shank 2, a respective instrument section 4 is articulated on this hollow shank in a pivotable manner over an angular range of essentially up to 90° transversely to a longitudinal axis of the hollow shank 4. In the region of the distal end of the instrument section 4, branches 6 of the gripper forceps represented in FIG. 1 and blades 8 of the scissors represented in FIG. 2 are mounted in a pivotably movable manner. The branches 6 or the blades 8 are coupled in movement to a handle 10, which is arranged on the proximal end of the hollow shank 2, by an actuator arranged in the instrument section 4 and the hollow shank 2, and this actuator will be discussed in more detail hereinafter. Moreover, a further actuator is arranged on the instrument section 4 and in the hollow shank 2, the further actuator being described in more detail hereinafter whereby the instrument section 4 may be pivoted relative to the hollow shank 2. These actuators are coupled in movement to an actuation lever 12, which is arranged on the proximal end of the hollow shank 2 in the region of the handle 10.

FIGS. 3 to 16, in an enlarged manner, show the connection of the instrument section 4 to the hollow shank 2 of the gripper forceps according to FIG. 1 or of the scissors according to FIG. 2. The hollow shank, at its distal end, forms a fork with two continuations 14. These continuations 14 are aligned in the longitudinal direction of the hollow shank 2 and are arranged diametrically opposite one another. A bore 16 is formed respectively on each of the continuations 14, wherein the bores 16 have a common central axis. The bores 16 serve for receiving joint pins, with which the pivotable instrument section 4, at a proximal end region arranged between the continuations 14, is pivotably connected to the hollow shank 2.

For pivoting the instrument section 4, an elongate actuator in the form of a slider 18, which is axially displaceably guided in the hollow shank 2 and which in the region of its proximal end is coupled in movement to the actuation lever 12, is arranged in the hollow shank 2. A lever 20 is articulated on the slider 18, close the distal end of this slider, via a joint pin 19. The lever 20, in the region of its end which is away from the articulation on the slider 18, is articulated on the pivotable instrument section 4 via a joint pin 42. A slot 22, which extends parallel to the central axis A of the hollow shank 2, is formed on the hollow shank 2, on a lower side lying directly opposite the slider 18 and the lever 20, proximally on the intermediate space formed between the continuations 14, in order to permit a sufficient pivot movement of the lever 20 transversely to the central axis A of the hollow shank 2.

An instrument part 24 is mounted in the pivotable instrument section 4 in a linearly movable manner in the axial direction of the instrument section 4. With regard to the instrument part 24, it is the case of a pull-push rod which is coupled in movement to a mechanism for pivoting the branches 6 of the gripper forceps represented in FIG. 1 or for pivoting the blades 8 of the scissors represented in FIG. 2, the mechanism not being represented and belonging to the state of the art.

For moving the instrument part 24, a further elongate actuator is arranged in the hollow shank 2, and this further actuator is formed by a slider 26, which is axially movably guided in the hollow shank 2. The instrument part 24, in the instrument section 4, is connected to this slider 26 in an articulated manner via a multi-joint arm 28. A first elongate arm part 30 of the multi-joint arm 28 is articulated on the slider 26 via a joint pin 31 in the region of the distal end of the slider 26. Two arm parts 32 are articulated on the arm part 30, in the region of the end of this arm part 30 away from the articulation on the slider 26, wherein the arm parts 32 are fastened on flat sides of the arm part 30 facing away from one another. An elongate arm part 34 is articulated between the arm parts 32 on the ends of the arm parts 32 away from the articulation on the arm part 30, and two arm parts 36, in the region of the end of the arm part 34 away from this articulation, are fastened on flat sides of the arm part 34 facing away from one another. Finally, a further arm part 38 is articulated between the arm parts 36, in the region of the ends of the arm parts 36 away from the articulation of the arm parts 36 on the arm part 34, and this further arm part 38 is connected to the instrument part 24 in a pivotably movable manner.

The two arm parts 32 as well as the two arm parts 36 are formed by plates which are rounded and are essentially rectangular in a plan view (FIGS. 11, 15), wherein a connection line of the articulation points to the arm parts 30 and 34 is arranged on the arm part 32 essentially parallel to a side edge of the arm part 32, and a connection line of the articulation points to the arm parts 34 and 38 is arranged on the arm part 36, essentially parallel to a side edge of the arm part 36. In the region of a corner, which is arranged essentially perpendicularly and spaced from the connection line of articulation points to adjacent arm parts, the arm parts 32 are pivotably fastened on the hollow shank 2 via a joint pin 40 (FIGS. 11 and 15), and the arm parts 36 on the instrument section 4 via a joint pin 42. The joint pin 42 serves further for articulation of the lever 20 on the instrument section 4. The instrument section 4 comprises a longitudinal slot 44 directly opposite the multi joint arm 28, in order to be able to deflect the arm parts 30, 32, 34 and 36 even beyond the inner contour of the instrument section 4 with a bending of the multi joint arm 28.

The manner of functioning of the mechanism represented in FIGS. 3 to 16 is as follows:

In order to pivot the instrument section 4 from the position represented in the FIGS. 3 to 8, in which the instrument section 4 forms a direct straight extension of the hollow shank 2, into the position represented in FIGS. 9 to 16, which is pivoted by approx. 90°, the slider 18 is pulled by the actuation lever 12 in the proximal direction, whereby the instrument section 4 is pivoted at an angle of approx. 90° by deflection of the lever 20. Simultaneously with the pivoting of the instrument section 4, the arm parts 32 are also pivoted about a pivot axis formed by the joint pin 40, and the arm parts 36 are pivoted about a pivot axis formed by the joint pin 42, whereby the multi-joint arm 28 changes its shape corresponding to the pivoting of the instrument section 4, without the instrument part 24, movably mounted in the instrument section 4, and the slider 26 being essentially moved. The pivoting of the instrument part 4 from the pivoted position represented in FIGS. 9 to 16, into the non-pivoted position, is effected in the reverse manner, by the slider 18 being moved in the distal direction by the actuation lever 12, whereby the instrument section 4 is pivoted by the lever 20 articulated on the slider 18 into a position in which it is arranged in the straight extension of the hollow shank 2.

The instrument part 24, which is movably mounted in the instrument section 4 and which is coupled in movement to the branches 6 of the gripper forceps represented in FIG. 1 or to the blades 8 of the scissors represented in FIG. 2, for opening and closing the forceps jaw or the scissors, may be displaced in the distal direction in the instrument section 4 by the slider 26 being pushed in the distal direction by actuating the handle 10, wherein the movement of the slider 26 is transmitted from the multi-joint arm 28 onto the instrument part 24. Reversely, the instrument part 24 may be displaced in the proximal direction, by the slider 26 being pulled in the proximal direction by actuating the handle 10. The design of the multi-joint arm 28 permits these movements in the distal as well as proximal direction, when the instrument section 4 is arranged in the direct straight extension of the hollow shank 2, as well as when the instrument section 4 is pivoted with respect to the hollow shank 2, thus in each intermediate position.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A medical instrument comprising:
 a hollow shank (2); and
 an instrument section (4) having an instrument part (24) mounted inside the instrument section (4), the instrument part (24) being linearly movable with respect to the instrument section (4) along an axial direction of the instrument section (4), the instrument section, proximate a distal end of the hollow shank (2), being arranged in a pivotable manner to the hollow shank (2),
 wherein the instrument part (24) is coupled in movement to a first actuator (26) which is axially movably guided in the hollow shank (2) via a forcibly guided multi-joint arm (28),
 wherein the multi-joint arm (28) comprises at least three arm parts (30, 32, 34, 36, 38) connected in series to one another in an articulated manner, wherein at least a second arm part (32), arranged between first and third arm parts (30, 34), is pivotable about a first axis (40) arranged on the hollow shank (2), the first axis (40) being spaced from a straight connection line of articulation points of the first and third arm parts (30, 34) to the second arm part (32).

2. The medical instrument according to claim 1, wherein at least a fourth arm part (36), arranged between the third arm part (34) and a fifth arm part (38), is pivotable about a second axis (42) arranged on the instrument section (4), the second axis (42) being spaced from a straight connection line of the articulation points of third and fifth arm parts (34, 38) to the fourth arm part (36).

3. The medical instrument according to claim 1, wherein a second actuator (18) is axially movably guided in the hollow shank (2), and wherein a lever (20) is articulated on a distal end region of the second actuator (18) and on the instrument section (4).

4. The medical instrument according to claim 1, wherein the distal end of the hollow shank (2) forms a fork on which the instrument section (4) is pivotably articulated.

5. The medical instrument according to claim 1, wherein a tube part forms an outer envelope of the instrument section (4).

6. The medical instrument according to claim 5, wherein the tube part has a longitudinal slot (44) in a region lying directly opposite the multi joint arm (24).

7. The medical instrument according to claim 1, wherein the instrument comprises a gripper forceps.

8. The medical instrument according to claim 1, wherein the instrument comprises a scissors.

9. The medical instrument according to claim 1, wherein the instrument comprises an organ manipulator.

* * * * *